United States Patent [19]

Mieno et al.

[11] 4,160,116

[45] Jul. 3, 1979

[54] PROCESS FOR THE PRODUCTION OF ALKYLENE GLYCOLS

[75] Inventors: Michihiro Mieno, Yokohama; Hideki Mori, Kawasaki; Jun Nakanishi; Juichi Kasai, both of Tokyo, all of Japan

[73] Assignee: Showa Denko K.K., Tokyo, Japan

[21] Appl. No.: 937,460

[22] Filed: Aug. 28, 1978

[51] Int. Cl.² ............................................. C07C 29/00
[52] U.S. Cl. .................................................... 568/867
[58] Field of Search ......................................... 568/867

[56] References Cited

FOREIGN PATENT DOCUMENTS 1177877  1/1970  United Kingdom .................... 568/867

*Primary Examiner*—Joseph E. Evans
*Attorney, Agent, or Firm*—Wenderoth, Lind & Ponack

[57] ABSTRACT

Process for the production of an alkylene glycol in which the hydration of an alkylene oxide is carried out in the presence of carbon dioxide using a quaternary phosphonium salt as a catalyst.

9 Claims, No Drawings

PROCESS FOR THE PRODUCTION OF ALKYLENE GLYCOLS

This invention relates to a process for the production of alkylene glycols by the hydration of alkylene oxides. More specifically, it relates to a process for the production of alkylene glycols by hydrating alkylene oxides in the presence of carbon dioxide using a quaternary phosphonium salt as a catalyst.

Methods have long been known for hydrating alkylene oxides, e.g. ethylene oxide or propylene oxide, to produce the corresponding alkylene glycols, e.g. ethylene glycol or propylene glycol. In these conventional liquid-phase hydration reactions, a very large quantity of water is used. Without the presence of a large quantity of water in the reaction system, the yield of the desired alkylene glycol would be low with the formation of considerably large amounts of by-products including the diglycol and triglycol. Accordingly, it is the usual practice to carry out the liquid-phase hydration reaction at a temperature of 100° to 200° C. using a large excess of water, for example 10 to 15 moles per mole of ethylene oxide when producing ethylene glycol from ethylene oxide, and 15 to 20 moles per mole of propylene oxide when producing propylene glycol from propylene oxide. Even when such a large excess of water is used, formation of no small amounts of the by-products diglycol and triglycol cannot be avoided. Since the amount of water is large, the reaction product is obtained as a considerably dilute aqueous solution, and vast energy and equipment are required to separate and purify the reaction product after the reaction.

In an attempt to overcome this difficulty of the prior art, a method has recently been suggested which involves hydrating an alkylene oxide in the presence of carbon dioxide to produce the corresponding alkylene glycol. According to this method, the alkylene oxide is reacted with water in the liquid phase in the presence of carbon dioxide and a catalyst at an elevated pressure of, say, up to 180 atmospheres, and an elevated temperature of, say, up to 220° C. The method does not require as much water as is necessitated by the prior art methods, and 1 to several moles, per mole of alkylene oxide, of water is sufficient. The amounts of by-products are small, and the desired alkylene glycol is obtained in concentrated form in high yields. However, since no good result is obtained without the use of catalyst, it is desired to find out good catalysts for this reaction.

Catalysts which have been suggested for use in the hydration of alkylene oxides in the presence of carbon dioxide include alkali metal halides such as chlorides, bromides and iodides of potassium, sodium and lithium, or quaternary ammonium halides such as tetramethylammonium iodide and tetraethylammonium bromide (British Pat. No. 1,177,877), and organic tertiary amines such as triethylamine and pyridine (German OLS No. 2,615,595). Generally, these catalysts give fairly good results. In the commercial-scale production of alkylene glycols, however, these catalysts suffer from various defects such as those described in (a) to (d) below. Accordingly, these catalysts are not entirely satisfactory, and no commercial production of alkylene glycol with these catalysts has been performed.

(a) Alkali metal halides tend to corrode the wall of a reactor in a reaction system containing water and maintained at an elevated temperature. This shortens the service life of the reaction apparatus, and an apparatus made of a special corrosion-resistant alloy must be used.

(b) Alkali metal halides and quaternary ammonium halides have a relatively low solubility in alkylene glycols, and therefore, are likely to precipitate as solids in the reaction system during the course of the reaction. Particularly, when separating the product from the reaction mixture, the catalyst deposits as a solid at the bottom of an evaporation device. It is considerably troublesome to remove the adhering catalyst from the bottom of the evaporator. Also, the adhering catalyst is difficult to recycle from the bottom to the reactor for re-use.

(c) As is well known, tertiary amines have a strong unpleasant smell. Such a smell is uncomfortable during handling, and persists in the resulting alkylene glycol. Unless some special purification technique is used, it is almost impossible to remove the smell completely from the alkylene glycol. The quaternary ammonium halides do not have so strong a smell, but will impart an unpleasant smell to the alkylene glycol product. Such smells markedly reduce the market value of the final product. This olfactory defect is especially serious when propylene glycol, for example, is used as an antiseptic aid for foodstuffs, a wetting agent for tobacco leaves, or additives for cosmetics and medicines.

(d) The starting alkylene oxide, depending upon its type, has a very low solubility in water. For example, 1 mole of propylene oxide cannot be completely dissolved in less than about 5 moles of water. In the hydration of alkylene oxide in the presence of carbon dioxide, water is used in an amount of 1 mole or slightly more per mole of alkylene oxide. Hence, the two components do not form a complete homogeneous solution, but phase separation occurs. The phase separation is advanced by the presence of carbon dioxide. The conventional known catalysts, i.e. alkali metal halides, quaternary ammonium halides and tertiary amines, further advance the phase separation of a mixture of propylene oxide and water. When propylene oxide is to be hydrated in the presence of carbon dioxide using these known catalysts, the separated liquid layer must be very vigorously stirred mechanically especially at the early stage of the reaction to disperse propylene oxide in water.

It has now been found that quaternary phosphonium salts can be effectively used as a catalyst in the hydration of alkylene oxides in the presence of carbon dioxide without involving the aforesaid defects of the conventional catalysts.

The quaternary phosphonium salts have no corrosive action nor offensive smells. They have a high solubility in the alkylene glycol, and a superior catalytic action on the hydration reaction. If the quaternary phosphonium salts are used as catalyst, the reaction can be performed under conditions which are equivalent to, or somewhat milder than, those used in the presence of the conventional catalysts. The quaternary phosphonium salts do not corrode the reaction apparatus, and can afford odorless alkylene glycols with good efficiency. Furthermore, the bottom residue containing the catalyst in solution which is left after the separation of the product can be directly recycled to the reactor for re-use.

It is especially noteworthy that the quaternary phosphonium salts do not advance the phase separation of a mixture of water and an alkylene oxide, e.g. propylene oxide, having a low solubility in water, but on the contrary, they surprisingly have an action of converting this mixture into a single homogeneous phase. For example, a mixture of 1 mole of propylene oxide and 1.1 moles of water separates into two liquid layers, and when any of the conventional catalysts is added to this system, the mixture remains separated and the phase separation is rather advanced. If, on the other hand, a small amount (e.g. 0.012 mole) of triphenylmethylphosphonium iodide is added as a catalyst, this mixture forms a complete homogeneous solution, and the catalyst also dissolves in it completely. The phenomenon of forming such a homogeneous solution is more surprising in view of the fact that the phosphonium iodide has a low solubility in water and propylene oxide and does not completely dissolve in any one of the water and propylene oxide in the aforesaid amounts. The quaternary phosphonium salts have varying solubilities in water and propylene oxide depending upon their types. Formation of a homogeneous solution described above occurs with all the quaternary phosphonium salts used as a catalyst in the present invention.

This phenomenon has been discovered for the first time by the present invention, and cannot be expected at all from the prior art. The mechanism of forming such a homogeneous solution has not yet been elucidated in detail, but it is theorized that it is based on the surface activating action of the quaternary phosphonium salt and/or the ability of the quaternary phosphonium salt to form a complex with the alkylene oxide. In any case, the formation of such a homogeneous solution has enabled the reaction of an alkylene oxide having a low solubility in water with water to be commercially performed advantageously over the prior art techniques. By adding a quaternary phsophonium salt as a catalyst, a mixture of propylene oxide and water as a homogeneous solution can be fed into a reactor without any difficulty. The reaction can be performed smoothly without performing vigorous mechanical stirring in the reactor. Accordingly, a tubular reactor can, for example, be used as the reactor, and the starting reactant solution can be passed through it to complete the reaction.

Preferred embodiments of the present invention are described below.

The quaternary phosphonium salt used as a catalyst in the production of an alkylene glycol by the hydration of an alkylene oxide in the presence of carbon dioxide in accordance with this invention is expressed by the following formula

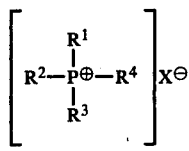 (I)

wherein $R^1$, $R^2$, $R^3$ and $R^4$, independently from each other, represent an alkyl, alkenyl or aryl group, and X represents an iodine, bromine or chlorine atom.

The quaternary phosphonium salt of the above formula can be prepared by a known method from a phosphine of the formula

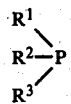

and a halide of the formula $R^4X$. From the standpoint of various practical aspects such as the ease of production and purification, the cost, and the activity and stability of the catalyst obtained, $R^1$, $R^2$ and $R^3$ preferably represent an acyclic or cyclic alkyl group of 1 to 8 carbon atoms, phenyl, tolyl, xylyl, or benzyl, and $R^4$ is preferably an acyclic or cyclic alkyl group of 1 to 18 carbon atoms, an alkenyl group of 2 to 3 carbon atoms, or benzyl.

Generally, quaternary phosphonium salts of the above formula in which X is iodine or bromine have higher catalytic activity than those of the above formula in which X is chlorine. When X is fluorine, the compounds show no satisfactory activity.

Examples of suitable catalysts used in this invention include the following:

Tripropylmethylphosphonium iodide,
tripropylethylphosphonium chloride,
tetrapropylphosphonium bromide,
tripropylbutylphosphonium iodide,
tripropyloctylphosphonium iodide,
tripropylcyclohexylphosphonium chloride,
tripropylphenylphosphonium bromide,
tributylmethylphosphonium iodide and bromide,
tributylethylphosphonium bromide,
tributylpropylphosphonium chloride,
tetrabutylphosphonium iodide,
tributylamylphosphonium bromide,
tributylhexylphosphonium chloride,
tributyloctylphosphonium iodide,
tributyldecylphosphonium bromide,
tributylcetylphosphonium iodide,
tributylbenzylphosphonium chloride,
tributylallylphosphonium chloride,
tributylcyclohexylphosphonium bromide,
triamylmethylphosphonium bromide,
triheptylbutylphosphonium chloride,
trihexylmethylphosphonium iodide,
trihexylbutylphosphonium bromide,
trihexyloctylphosphonium chloride,
trioctylmethylphosphonium iodide and bromide,
trioctylethylphosphonium bromide,
trioctylpropylphosphonium chloride,
trioctylbutylphosphonium iodide,
trioctylamylphosphonium bromide,
tetraoctylphosphonium chloride,
trioctylcetylphosphonium iodide,
trioctylbenzylphosphonium chloride,
triphenylmethylphosphonium iodide,
triphenylpropylphosphonium bromide,
triphenylbutylphosphonium iodide,
triphenylheptylphosphonium bromide,
triphenylbenzylphosphonium chloride,
tritolylmethylphosphonium iodide,
trixylylbenzylphosphonium bromide,
tribenzylethylphosphonium chloride,
tricyclohexylmethylphosphonium iodide,
tricyclopentylisobutylphosphonium chloride,
dimethylethylphenylphosphonium iodide, and
dibutylphenylmethylphosphonium iodide.

The amount of the quaternary phosphonium salt used is at least 0.001 mole%, preferably at least 0.01 mole%, based on the starting alkylene oxide. Although the reaction is more promoted as the amount of the catalyst is larger, the effect is not directly proportional to the amount of the catalyst. In practice, therefore, the catalyst is used in an amount of 0.001 mole% to the amount of saturation with regard to the reactant mixture, preferably 0.01 to 10 mole%.

The starting alkylene oxide is a lower alkylene oxide having 2 to 4 carbon atoms, especially ethylene oxide and propylene oxide.

The amount of water fed is sufficiently a stoichiometrical amount based on the alkylene oxide. In actual commercial practice, it is convenient to use water in an amount somewhat larger than the stoichiometrical amount and up to about 4.0 times as large as it.

The amount of carbon dioxide is not necessarily critical. Usually, however, it is 0.05 to 1 mole, preferably 0.1 to 0.5 mole, per mole of the alkylene oxide.

The reaction temperature, which varies depending upon the type of the starting alkylene oxide, the type of the catalyst, the composition of the reactant mixture at the early stage of the reaction, etc., is generally 50 to 200° C., preferably 110° to 160° C. The reaction pressure, which varies according to the amount of carbon dioxide, the reaction temperature, and the extent of advance of the reaction, is generally 3 to 50 kg/cm$^2$. If desired, the pressure within the reactor may be adjusted occasionally. The reaction time is about 30 minutes to about 3 hours.

The reaction proceeds smoothly by merely contacting the starting alkylene oxide, water, carbon dioxide and catalyst intimately under the aforesaid conditions, and gives an odorless alkylene glycol in a high yield. In commercial practice, the reaction can be advantageously carried out by a continuous process. One embodiment of the commercial operation is as follows: Predetermined amounts of the starting water and alkylene oxide and the quaternary phosphonium salt as a catalysts are mixed in a mixing tank. The mixture which has become a homogeneous solution by the presence of the catalyst is continuously fed into a tubular reactor kept at a predetermined temperature, and passed through it. Carbon dioxide can be introduced into the mixing tank, or into the mixture in transit through a pipe by using a line mixer. The reaction mixture from the reactor is sent to an evaporator where the water and the resulting alkylene glycol are evaporated to obtain a crude alkylene glycol. The crude alkylene glycol is subjected to a purifying step to obtain a high purity product. At the bottom of the evaporator, the used catalyst remains in the form of a solution in a small amount of alkylene glycol. The solution is recycled to the material mixing tank for re-use. Thus, the reaction can be continuously carried out without a loss of the catalyst.

The following laboratory-scale Examples are given to illustrate the present invention.

EXAMPLE 1

A 100 ml autoclave equipped with a thermometer, a pressure gauge and a stirrer was charged with 31.5 g of propylene oxide and 20.2 g of water. At this time, the liquid separated into two layers. When 4.4 g of tributylmethylphosphonium iodide was added, it dissolved and together with the separated layers, formed a homogeneous solution. Carbon dioxide was fed from a bomb to a pressure of 4.0 g/cm$^2$.G. The mixture was heated by a heater to 155° C., and reacted at this temperature for 2 hours. The pressure inside the reactor first rose to 10.6 kg/cm$^2$.G, then fell down to 6.0 kg/cm$^2$.G, and again went up. At the end of the reaction, it was 12.0 kg/cm$^2$.G. The reaction mixture was colorless, clear and odorless. The results of its analysis were as follows.

| | |
|---|---|
| Conversion of propylene oxide: | nearly 100% |
| Selectivity: | |
| to propylene glycol | 94.8% |
| to dipropylene glycol | 2.3% |
| to tripropylene glycol | 0.1% |

EXAMPLE 2

A 100 ml autoclave equipped with a thermometer, a pressure gauge and a stirrer was charged with 30.8 g of ethylene oxide, 25.2 g of water, and 6.54 g of triphenylmethylphosphonium iodide. Carbon dioxide was fed from a bomb to a pressure of 4.0 kg/cm$^2$.G. The mixture was heated by a heater to 150° C., and reacted at this temperature for 2 hours. The pressure inside the reactor first rose to 6.5 kg/cm$^2$.G, then fell down to 5.8 kg/cm$^2$.G, and again rose. At the end of the reaction, it was 11.2 kg/cm$^2$.G. The reaction mixture obtained was colorless, clear and odorless. The results of its analysis were as follows:

| | |
|---|---|
| Conversion of ethylene oxide: | 98.7% |
| Selectivity: | |
| to ethylene glycol | 95.7% |
| to diethylene glycol | 1.8% |
| to triethylene glycol | 0.13% |

EXAMPLE 3

The procedure of Example 2 was repeated except that 9.6 g of triphenylpropylphosphonium bromide was used as the catalyst. The reaction mixture obtained was colorless, clear, and odorless. The results of its analysis were as follows:

| | |
|---|---|
| Conversion of ethylene oxide: | 98.9% |
| Selectivity: | |
| to ethylene glycol | 91.9% |
| to diethylene glycol | 3.4% |
| to triethylene glycol | 0.25% |

EXAMPLE 4

The procedure of Example 1 was repeated except that 9.95 g of triphenylbenzylphosphonium chloride was used as the catalyst. The maximum pressure attained was 10.5 kg/cm$^2$.G. The resulting reaction mixture was colorless, clear, and odorless. The results of analysis were as follows:

| | |
|---|---|
| Conversion of propylene oxide: | 99.8% |
| Selectivity: | |
| to propylene glycol | 91.2% |
| to dipropylene glycol | 2.9% |
| to tripropylene glycol | 0.18% |

EXAMPLES 5 TO 8

The procedure of Example 1 was repeated except that triphenylmethylphosphonium iodide was used as the catalyst in an amount of 10.2 g, 5.16 g, 2.65 g, and 1.01 g, respectively. The resulting reaction mixture was colorless and odorless in each case. The results of analysis were tabulated below.

| Example | Conversion of propylene oxide (%) | Selectivity (%) to | | |
|---|---|---|---|---|
| | | Propylene glycol | Dipropylene glycol | Tripropylene glycol |
| 5 | nearly 100 | 94.1 | 2.0 | 0.11 |
| 6 | nearly 100 | 93.6 | 3.55 | 0.23 |
| 7 | 99.1 | 91.2 | 5.60 | 0.35 |
| 8 | 98.4 | 88.1 | 8.64 | 0.47 |

EXAMPLES 9 TO 12

The procedure of Example 2 was repeated except that 6.54 g of each of tetrabutylphosphonium iodide (Example 9), trioctylmethylphosphonium iodide (Example 10), trioctylbutylphosphonium iodide (Example 11), and trimethylcetylphosphonium bromide (Example 12) was used. The resulting reaction mixture was colorless, clear and odorless in each case, and variations in pressure showed a similar behavior to that in Example 1. The results of analysis are tabulated below.

| Example | Conversion of ethylene oxide (%) | Selectivity (%) to | | |
|---|---|---|---|---|
| | | Ethylene glycol | Diethylene glycol | Triethylene glycol |
| 9 | nearly 100 | 96.1 | 1.77 | 0.14 |
| 10 | nearly 100 | 94.7 | 2.05 | 0.16 |
| 11 | nearly 100 | 94.2 | 2.4 | 0.21 |
| 12 | 98.7 | 91.8 | 2.9 | 0.22 |

Comparative Example 1

A 300 ml autoclave equipped with a stirrer was cooled sufficiently with a dry ice bath, and then charged with 74 g of propylene oxide and 34 g of water. Further, 16 g of dry ice was added. The autoclave was then placed in an oil bath heated at 140° C., and the reaction was performed for more than 2 hours. The pressure inside the reactor gradually rose from the initial 2.5 kg/cm$^2$.G, and reached 32 kg/cm$^2$.G at a maximum. No drop in pressure was seen. The reaction mixture obtained had a smell of propylene oxide and a low viscosity, and was colorless.

The conversion of propylene oxide was 66.7%. The selectivities to propylene glycol, dipropylene glycol, and tripropylene glycol were 76.2%, 14.7%, and 0.6%, respectively. Furthermore, 8.0% of low-boiling compounds were formed.

What we claim is:

1. A process for the production of an alkylene glycol, in which the hydration of an alkylene oxide is carried out at a temperature of from 50° C. to 200° C. in the presence of 0.05 to 1.0 mole, per mole of alkylene oxide, of carbon dioxide and in the presence of, as a catalyst, a quaternary phosphonium salt of the formula

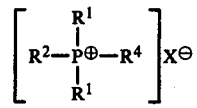

wherein R$^1$, R$^2$, R$^3$ and R$^4$, independently from each other, represent an alkyl, alkenyl or aryl group, and X represents an iodine, bromine or chlorine atom.

2. The process of claim 1 wherein in the formula expressing the quaternary phosphonium salt, R$^1$, R$^2$ and R$^3$ represent an acyclic or cyclic alkyl group having 1 to 8 carbon atoms, a phenyl group, a tolyl group, a xylyl group or a benzyl group, and R$^4$ represents an acyclic or cyclic alkyl group having 1 to 18 carbon atoms, an alkenyl group having 2 to 3 carbon atoms, or a benzyl group.

3. The process of claim 1 wherein the amount of the quaternary phosphonium salt is at least 0.001 mole% based on the alkylene oxide.

4. The process of claim 1 wherein the amount of the quaternary phosphonium salt is 0.01 to 10 mole% based on the alkylene oxide.

5. The process of claim 1 wherein the amount of water supplied for the hydration of the alkylene oxide is 1 to 4.0 moles per mole of the alkylene oxide.

6. The process of claim 1 wherein the amount of the carbon dioxide fed is 0.05 to 1 mole per mole of the alkylene oxide.

7. The process of claim 1 wherein the amount of the carbon dioxide fed is 0.1 to 0.5 mole per mole of the alkylene oxide.

8. The process of claim 1 wherein the reaction temperature is 110 to 160° C.

9. The process of claim 1 wherein the reaction pressure is 3 to 50 kg/cm$^2$.